United States Patent
Wang et al.

(10) Patent No.: US 9,346,770 B2
(45) Date of Patent: May 24, 2016

(54) COMPOUNDS HAVING ACTIVATING EFFECT ON SUBTYPES OF PEROXISOME PROLIFERATOR-ACTIVATED RECEPTORS AND ITS PREPARATION METHOD AND USES

(75) Inventors: Yaping Wang, Shanghai (CN); Guojun Zheng, Shanghai (CN); Peng Sun, Shanghai (CN); Yi Li, Shanghai (CN); Yingqiu Wu, Shanghai (CN); Bin Liu, Shanghai (CN); Xiaoyu Liu, Zhejiang (CN); Hua Bai, Zhejiang (CN); Hongyan Li, Zhejiang (CN); Xiaohe Zheng, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 13/704,281

(22) PCT Filed: Jun. 18, 2011

(86) PCT No.: PCT/CN2011/075905
§ 371 (c)(1),
(2), (4) Date: Dec. 19, 2012

(87) PCT Pub. No.: WO2011/157227
PCT Pub. Date: Dec. 22, 2011

(65) Prior Publication Data
US 2013/0089613 A1 Apr. 11, 2013

(30) Foreign Application Priority Data

Jun. 18, 2010 (CN) .......................... 2010 1 0202120

(51) Int. Cl.
*C07D 263/32* (2006.01)
*A61K 31/421* (2006.01)
*C07D 413/10* (2006.01)
*C07D 277/24* (2006.01)
*A61K 31/439* (2006.01)

(52) U.S. Cl.
CPC ............ *C07D 263/32* (2013.01); *A61K 31/439* (2013.01); *C07D 277/24* (2013.01); *C07D 413/10* (2013.01)

(58) Field of Classification Search
None
See application file for complete search history.

(56) References Cited

U.S. PATENT DOCUMENTS

| 7,259,175 | B2 * | 8/2007 | Conner et al. | ............... 514/342 |
|---|---|---|---|---|
| 2003/0203947 | A1 | 10/2003 | Chao et al. | |
| 2010/0063041 | A1 | 3/2010 | Moon et al. | |

FOREIGN PATENT DOCUMENTS

| EP | 1 666 472 A1 | 6/2006 |
|---|---|---|
| WO | 03/072102 A1 | 9/2003 |
| WO | 2004/031162 A1 | 4/2004 |
| WO | 2007/030567 A2 | 3/2007 |
| WO | 2007/056366 A2 | 5/2007 |

OTHER PUBLICATIONS

Grundy et al. Circulation 112 (2005), p. 2745, first paragraph.*
American Heart Association, "Metabolic Syndrome" Mar. 30, 2009, <http://www.americanheart.org/presenter.jhtml?identifier=4756>.*
Mathur, "Metabolic Syndrome," Mar. 31, 2009, <http://www.medicinenet.com/metabolic_syndrome/article.htm>.*
Molnar ("New drug policy in childhood obesity," 2005, International Journal of Obesity, 29:S62-S65).*
PCT International Search Report for PCT/CN2011/075905 mailed Sep. 29, 2011.
European Communication for EP Application No. 11 795 193.9 mailed Dec. 23, 2014 (6 pages).
Response to European Communication for EP Application No. 11 795 193.9 mailed May 1, 2015 (5 pages).

* cited by examiner

*Primary Examiner* — Alicia L Otton
(74) *Attorney, Agent, or Firm* — Sutherland Asbill & Brennan LLP

(57) ABSTRACT

Phenyl propanoic acid compounds having activating effect on peroxisome proliferator-activated receptors (PPARα,δ,γ) and a preparation method and uses thereof are provided in the present invention. The compounds can be used for treating or preventing diseases associated with peroxisome proliferator-activated receptors (PPARα,δ,γ).

7 Claims, No Drawings

COMPOUNDS HAVING ACTIVATING EFFECT ON SUBTYPES OF PEROXISOME PROLIFERATOR-ACTIVATED RECEPTORS AND ITS PREPARATION METHOD AND USES

CROSS REFERENCE TO RELATED APPLICATIONS

This application is a national phase of PCT/CN2011/075905 filed on Jun. 18, 2011, which claims priority of Chinese Application No. 201010202120.1 filed on Jun. 18, 2010. The contents of these applications are hereby incorporated by reference in their entirety.

TECHNICAL FIELD

The present invention relates to novel compounds having activating effect on a subtype, δ subtype, and γ subtype of peroxisome proliferator-activated receptors (PPARs), preparation method thereof, and use of the medicaments comprising the same in the treatment of diabetes and cardiovascular diseases. The present invention also relates to intermediates of the novel compounds and preparation method thereof.

BACKGROUND OF THE INVENTION

With the development of productivity and quality of life, metabolic syndrome, characterized by obesity, anti-insulin (type II diabetes), lipid metabolism disorder, and hypertension, occurs throughout the world, and threatens human health greatly due to excessive intake of fats and proteins, In addition to association with the genetic characteristics, age, sex, physiological characteristics, nutritional status, diet habits, etc. of individuals, metabolism syndrome is also involved in the broken of balances of lipid metabolism, energy, and carbohydrate metabolism in vivo. Thus, a therapeutic regimen aiming to maintain the balances of energy, fats and carbohydrates in vivo becomes an effective method for treating metabolism syndrome. Nuclear receptors (NRs) tends to a focus of researches as it plays a critical role in maintaining the balance of energy, and the balances of fats and carbohydrates in cells, even in the whole individual. Nuclear receptors can regulate transcription systems of responsive genes, and thus exerting their physiological activity only after being activated by various physiological ligands (e.g. saturated and unsaturated fatty acids, metabolites and various synthetic compounds thereof) (Kasuga, J. et al., *Bioorg. Med. Chem.* 2007, 15, 5177-5190).

In the family of nuclear receptors, peroxisome proliferator-activated receptors (PPARs), nuclear transcription factors activated by ligands, have attracted the attention from the researchers for more than ten years, and are important regulatory factors in metabolism syndrome (Guan, Y. *J. Am. Soc. Nephrol,* 2004, 15, 2801-2815). Therefore, PPARs play an important role in the pathogenesis, development, treatment, and prevention of diseases, e.g. insulin resistance, impaired glucose tolerance, type II diabetes, obesity, hyperlipidemia, hypertension, cardiovascular diseases, artherosclerosis, etc.

PPARs are classified into three subtypes: PPARα, PPARδ, and PPARγ, which regulate expression of gene by binding to specific DNA sequences (Berger, J. et al., *The Journal of Biological Chemistry,* 1999, 274 (10), 6718-6725). PPARα is mainly expressed in liver, heart, intestinal tract, kidney, and macrophage, and can increase the metabolism of fatty acids, alleviate inflammatory response of macrophage, and reduce low density lipoprotein cholesterol, after being activated; PPARγ is expressed in adipocyte, placentoma, and other tissues, and not only can reduce blood glucose and increase insulin sensitivity but also plays a critical role in lipid metabolism, cytokine inhibition, anti-inflammation, immune regulation, blood pressure regulation, etc., after being activated (Kasuga, J. et al., *Bioorg. Med. Chem.* 2007, 15, 5177-5190). Relative to the other two subtypes, the physiological function of PPARδ is unknown so far. However, recent researches on animal models for pharmacology experiments show that PPARδ can increase the catabolism of fatty acid and energy uncoupling in adipose tissues and muscles, and inhibit macrophage-derived inflammation. By controlling weight gain, increasing tolerance of human body, increasing insulin sensitivity, and improving artherosclerosis in various aspects, ligands of PPARδ may thus become an effective medicament for treating hyperlipidemia, obesity, insulin resistance, and artherosclerosis.

Nowadays, none of "three channel" agonist having effect on all of PPARα, PPARδ, and PPARγ is commercially available as a therapeutic agent throughout the world. The "three channel" agonist of PPARα, PPARδ, and PPARγ developed by the inventors can be used in the treatment of metabolism syndrome which is mainly characterized by diabetes. It has a similar function as glitazones or other insulin sensitizers, but can be applied more widely. Although PPARγ agonists, glitazones can increase the sensitivity to insulin, recent clinical results show that it might increase the risk of cardiovascular diseases. Moreover, glitazones have further common side effects, including weight gain and liver toxicity. Therefore, the inventors make great efforts to find a novel medicament which not only can treat diabetes but also have a certain protection effect on cardiovascular.

The research and development of novel medicaments for metabolism syndrome have been a focus in many pharmaceutical companies. Chinese pharmaceutical companies are also competitively focusing their researches on new targets in the development of medicines for diabetes. Therefore, it will be of great clinical significance to provide novel compounds having activating effect on peroxisome proliferator-activated receptors (PPARα, PPARδ, and PPARγ).

SUMMARY OF THE INVENTION

One object of the present invention is to provide a compound of formula I or pharmaceutically acceptable salts thereof:

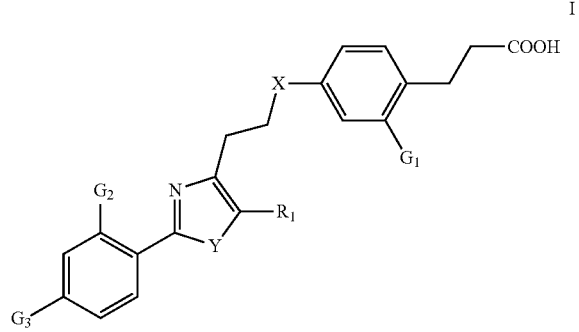

wherein,

X is O, S, $NR_{11}$, or $(CR_{11}R_{11'})_n$, in which n is an integer selected from 1, 2, 3 and 4;

Y is O, S, $NR_{11}$, or $(CR_{11}R_{11'})_m$, in which m is an integer selected from 1, 2, 3 and 4;

$R_1$ is independently H, alkyl, or cycloalkyl;

$G_1$ is independently alkyl, or cycloalkyl;

$G_2$ and $G_3$ are each independently selected from H, alkyl, alkoxy, trifluoromethyl, halogen (F, Cl, Br), nitro, $NR_{11}R_{11'}$, alkylthio, amido, cyano, carboxyl and tetrazolyl;

$R_{11}$ and $R_{11'}$ are each independently selected from H and $C_1$-$C_6$ alkyl.

In a preferred compound of formula I, X is S, O, or $NR_{11}$, Y is O, and other substituents are as defined above.

In another preferred compound of formula I, $R_1$ is independently H or $C_1$-$C_6$ alkyl, and other substituents are as defined above.

In another preferred compound of formula I, $G_1$ is selected from $C_1$-$C_6$ alkyl, and other substituents are as defined above.

In another preferred compound of formula I, $G_2$ and $G_3$ are each independently selected from H, $C_1$-$C_6$ alkyl, $C_1$-$C_6$ alkoxy, trifluoromethyl, F, Cl, Br, nitro, $NR_{11}R_{11'}$, $C_1$-$C_6$ alkylthio, amido, cyano, carboxyl and tetrazolyl, and other substituents are as defined above.

In another preferred compound of formula I, $G_1$ is ethyl; $G_2$, $G_3$ are F, $CF_3$ or methyl, and other substituents are as defined above.

In another preferred compound of formula I, $R_1$ is methyl or H, and other substituents are as defined above.

The following compounds of formula I or pharmaceutically acceptable salts thereof are more preferred:

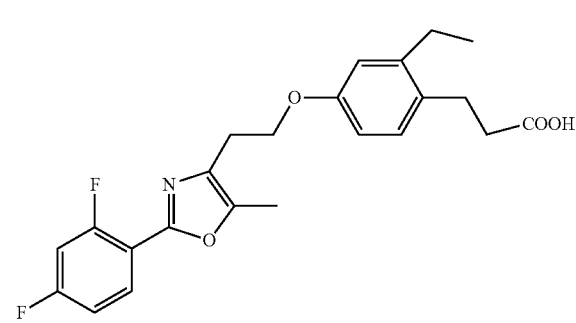

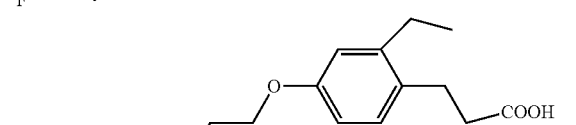

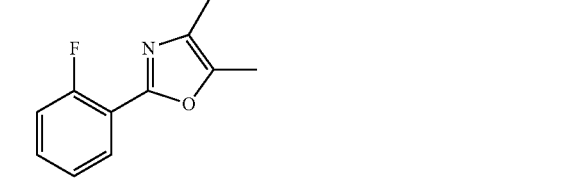

-continued

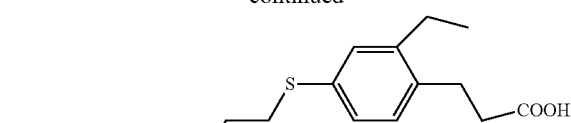

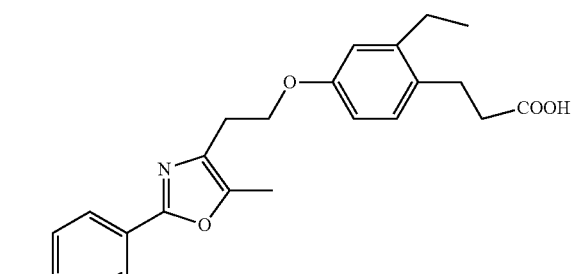

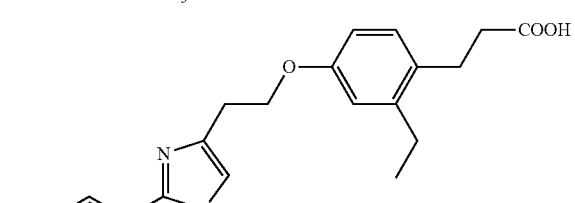

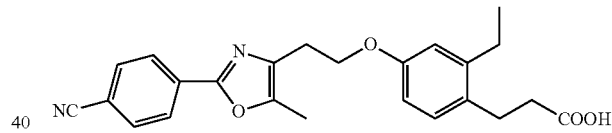

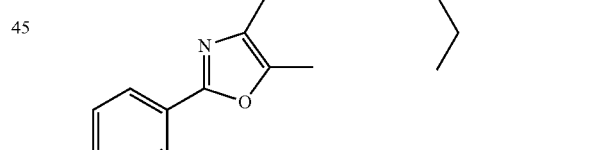

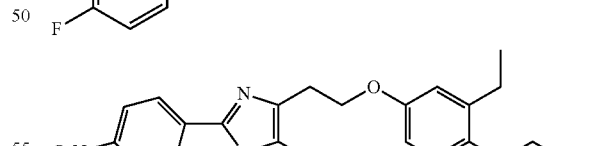

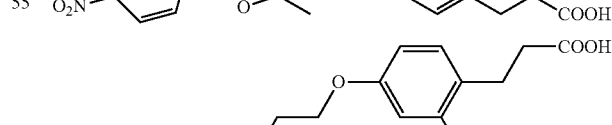

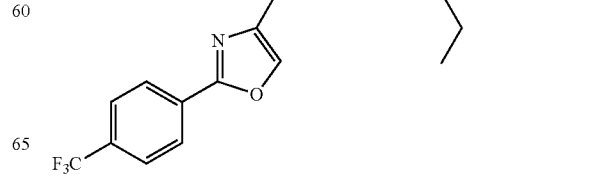

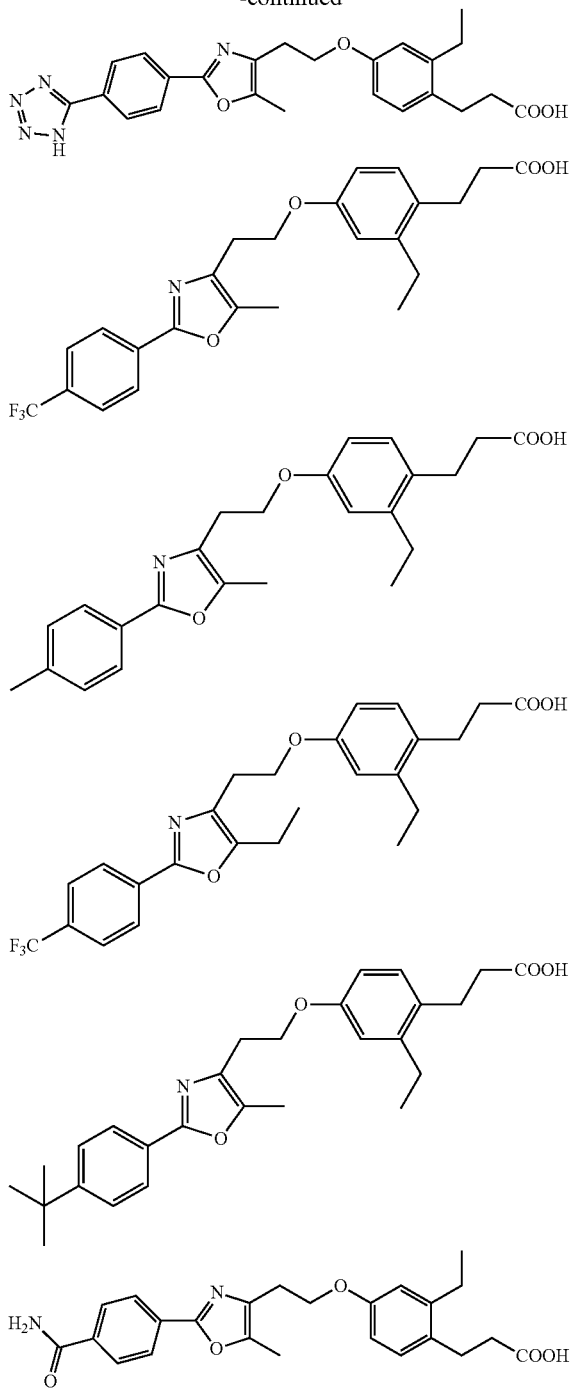

As used herein, the term "alkyl" refers to a monovalent linear or branched saturated aliphatic hydrocarbon group having carbon atoms within a certain range. As such, e.g. "$C_{1-6}$ alkyl" (or "$C_1$-$C_6$ alkyl") refers to any isomer of hexyl and pentyl; n-butyl, iso-butyl, sec-butyl, and t-butyl; n-propyl and iso-propyl; ethyl; and methyl. As a further example, "$C_{1-4}$ alkyl" refers to n-butyl, iso-butyl, sec-butyl, and t-butyl; n-propyl and iso-propyl; ethyl; and methyl.

The term "alkenyl" refers to a monovalent linear or branched aliphatic hydrocarbon group having one carbon-carbon double bond and having carbon atoms within a certain range. As such, e.g. "$C_{2-6}$ alkenyl" (or "$C_{2-6}$ alkenyl") refers to all isomers of hexenyl and pentenyl; 1-butenyl, 2-butenyl, 3-butenyl, iso-butenyl; 1-propenyl, 2-propenyl; and ethenyl. As for the present invention, alkenyl is advantageously those of formula —CH═CH—$(CH_2)_{1-3}CH_3$.

The term "alkynyl" refers to a monovalent linear or branched aliphatic hydrocarbon group having one carbon-carbon triple bond and having carbon atoms within a certain range. As such, e.g. "$C_2$-$C_6$ alkynyl" (or "$C_{2-6}$ alkynyl") refers to all isomers of hexynyl and pentynyl; 1-butynyl, 2-butynyl, 3-butynyl; 1-propynyl, 2-propynyl; and ethynyl.

The term "alkylene" refers to a divalent linear or branched aliphatic hydrocarbon group having carbon atoms within a certain range. As such, e.g. "—$C_{1-6}$ alkylene-" refers to any $C_1$-$C_6$ linear or branched alkylene, and "—$C_{1-4}$ alkylene-" refers to any $C_1$-$C_4$ linear or branched alkylene. As for the present invention, alkylene is advantageously —$(CH_2)_{1-6}$—. More advantageously, alkylene includes —$(CH_2)_{1-4}$—, —$(CH_2)_{2-4}$—, —$(CH_2)_{1-3}$—, —$(CH_2)_{2-3}$—, —$(CH_2)_{1-2}$— and —$CH_2$—. Further advantageously, alkylene is selected from —$CH_2$—, —$CH(CH_3)$— and —$C(CH_3)_2$—.

The term "cycloalkyl" refers to any monocyclic alkane having carbon atom numbers within a certain range. As such, e.g. "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "cycloalkenyl" refers any monocyclic alkene having carbon atom numbers within a certain range. As such, e.g. "$C_{5-8}$ cycloalkenyl" (or "$C_5$-$C_8$ cycloalkenyl") refers to cyclopentenyl, cyclohexenyl, cycloheptenyl, and cyclooctenyl.

The term "halogen" (or "halo") refers to fluorine, chlorine, bromine and iodine.

The term "haloalkyl" refers to an alkyl as defined above, in which one or more hydrogen atom has been replaced by halogen (i.e. F, Cl, Br, and/or I). As such, e.g. "$C_{1-6}$ haloalkyl" (or "$C_1$-$C_6$ halogenated alkyl") refers to $C_1$-$C_6$ linear or branched alkyl as defined above having one or more halogen as the substituents. The term "fluoroalkyl" has a similar definition as above, except that the halogen substituent is defined to fluoro. Suitable fluoroalkyl includes a series of $(CH_2)_{0-4}CF_3$ (i.e. trifluoromethyl, 2,2,2-trifluoroethyl, 3,3,3-trifluoro-n-propyl, etc.). More advantageously, fluoroalkyl is $CF_3$.

The compound can be administered in the form of pharmaceutically acceptable salt thereof. The term "pharmaceutically acceptable salt" refers to a salt, which has the efficiency of its parent compound but does not exert undesired biological properties or undesired properties in other aspects (i.e., which is non-toxic and harmless to a subject). Suitable salts include acid addition salts, which can be, e.g., formed by mixing a solution of the compound of the present invention and a solution of pharmaceutically acceptable acids (such as hydrochloric acid, sulfuric acid, acetic acid, or benzoic acid). In the case that the compound used in the present invention carries an acidic moiety (such as —COOH or a phenolic group), its suitable pharmaceutically acceptable salt can include alkali metal salts (such as sodium salts or potassium salts), alkali earth metal salts (such as calcium salts or magnesium salts), and the salts formed from the compound and suitable organic ligands (such as quaternary ammonium salts). Furthermore, in the presence of an acid group (—COOH) or an alcohol group, a pharmaceutically acceptable ester can be applied, in order to improve the solubility or hydrolysis properties of the compound.

A further object of the present invention is to provide a pharmaceutical composition comprising the compound of formula (I). Wherein the dosage form of the pharmaceutical composition is selected from the following dosage forms: tablets, film-coated tablets, sugar coated tablets, enteric coated tablets, dispersible tablets, capsules, granules, oral solutions and oral suspensions.

A further object of the present invention is to provide a method for treating diseases associated with α subtype, δ subtype, and γ subtype of peroxisome proliferator-activated receptors (PPARα, PPARδ, and PPARγ). Wherein, the diseases associated with α subtype, δ subtype, and γ subtype of peroxisome proliferator-activated receptors (PPARα, PPARδ, and PPARγ) are selected from hyperglycaemia, insulin resistance, hyperlipidemia, obesity, etc.

In the treatment method according to the present invention, the compound of formula I, optionally in the form of its salt or prodrug, can be administered as a single therapeutic agent or a combination of therapeutic agents, by any applicable conventional method. Although can be administered separately, it is conventionally administered in combination with pharmaceutical vehicles which are selected according to the chosen route of administration and standard pharmaceutical practice. The compound according to the present invention can be, e.g., administered orally, parenterally (including subcutaneous injection, intravenous injection, intramuscular injection, intrasternal injection, or infusion), by inhalation spray, or rectally, in the form of a unit dose of a medicament comprising an effective amount of the compound and non-toxic conventional pharmaceutically acceptable vehicles, adjuvants, and excipients. Liquid dosage forms suitable for oral administration (such as suspensions, syrups, elixir, etc.) can be formulated according to any process known in the art, using any conventional medium, such as water, glycols, oils, alcohols, etc. Solid formulations suitable for oral administration (such as powders, pills, capsules, and tablets) can be formulated according to a process known in the art, using solid excipients, such as starch, sugars, kaolin, lubricants, binders, disintegrating agents, etc. Parenteral compositions can be formulated according to a process known in the art, conventionally using sterilized water, as the vehicle, and optionally other components such as cosolvents. Injectable solutions can be formulated according to a process known in the art, in which the vehicle includes saline solutions, glucose solutions, or solutions comprising the mixture of saline and glucose. A further description of the method suitable for the preparation of the pharmaceutical composition in the present invention and the components suitable for being used in the composition can be found from Remington's Pharmaceutical Sciences, 18th Edition, Edited by A. R. Gennaro, Mack Publishing Co., 1990 and Remington—The Science and Practice of Pharmacy, 21st Edition, Lippincott Williams & Wilkins, 2005.

A further object of the present invention is to provide a method for the preparation of a compound of formula (I), with referenced to the following scheme.

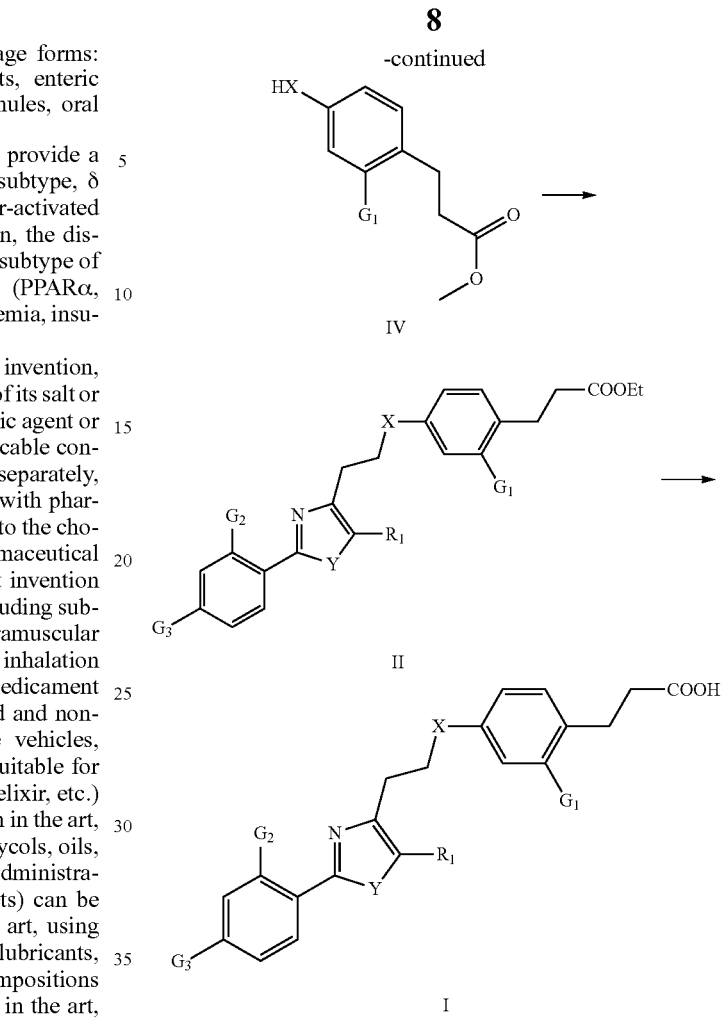

wherein,

X, Y, $R_1$, $G_1$, $G_2$, and $G_3$ are as defined in the compound of formula I, $R_3$ is a leaving group selected from OH, Cl, Br, I, OTs, OMs, etc.

Preferably, alkyl, alkoxyl, and alkylthio according to the present invention have 1-6 carbon atoms; and cycloalkyl has 3-8 carbon atoms.

In a preferred embodiment of the present invention, the preparation method includes: heating compound III and compound IV in acetonitrile under reflux in the presence of potassium carbonate, in order to obtain compound II; saponifying compound II in an alcoholic solution in the presence of an alkali; and acidifying the reaction mixture after the reaction is completed, in order to obtain target compound I.

Wherein, compound IV can be prepared according to the disclosure in the patent reference WO/2005/054176, with the following scheme:

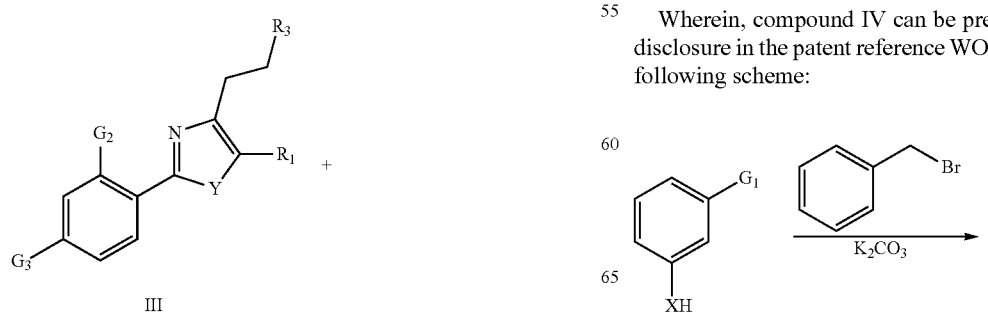

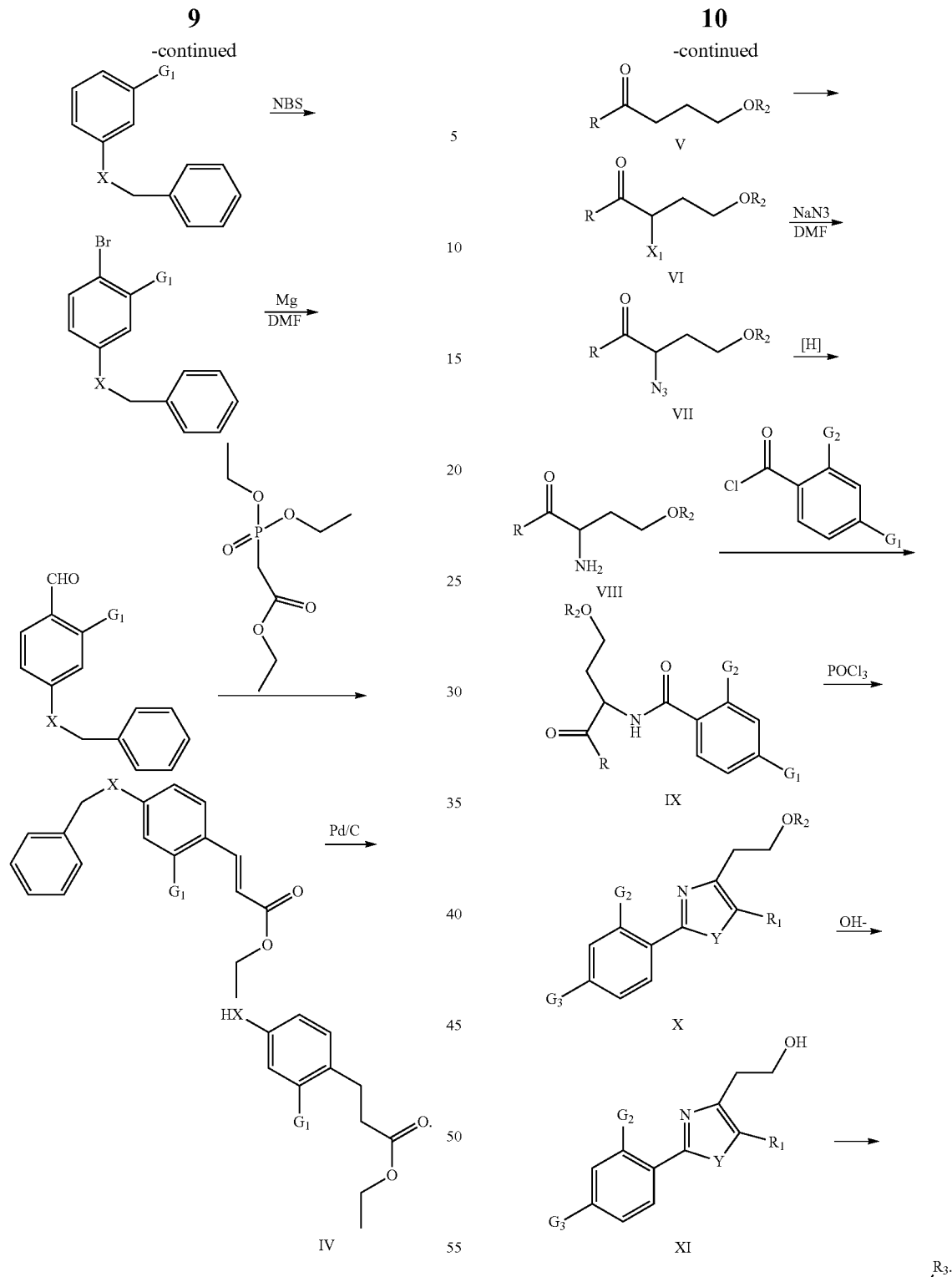
A further object of the present invention is to provide a method for the preparation of a compound of formula III, with the following scheme:
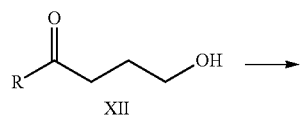

wherein R=H or $C_1$-$C_6$ alkyl; X=leaving group selected from Cl, Br, I, OTs, OMs, etc.; $R_2$=hydroxyl protective group; $R_3$=leaving group selected from Cl, Br, I, OTs, OMs, etc.

Compound XII, as the starting material, is subjected to hydroxyl protection, and then halogen or hydroxyl (can be converted into sulfonate) is introduced thereon at the α-position of the acyl substituent, in order to form a leaving group. Then, the product obtained is reacted with $NaN_3$, to form an azide. The azide is subjected to hydrogenation to obtain an amine, and then is reacted with corresponding acyl chloride, in order to obtain an amide. The amide is treated with phosphorus oxychloride, in order to obtain the cyclization product. The hydroxyl protective group is removed from the cyclization product, and the deprotected hydroxyl was converted into halogen or sulfate, in order to obtain compound III.

Drug Screening Model

The experimental procedure of the drug screening model is conducted as follows:

1). Brief Description of a Nuclear Receptor-Associated Screening Model

Using a reporter gene method, a screening model for screening a nuclear receptor agonist in living cells is designed on the basis of the principal that a nuclear receptor can activate transcription of its downstream gene after being activated. A reporter gene plasmid is constructed, in which the DNA binding sequence for the nuclear receptor (NRE) is inserted at the upstream of a luciferase gene, such that the expression of the luciferase gene is regulated by the nuclear receptor. The reporter gene plasmid is transferred into a cell simultaneously with the nuclear receptor. The nuclear receptor will be activated when a nuclear receptor agonist presents in the cell culture medium. The receptor being activated can induce the expression of the luciferase gene, while the amount of generated luciferase can be determined with its luminescent substrate. In this way, the intensity of activation of the nuclear receptor by the compound can be determined by observing the luminescence intensity. For the calibration of the experimental error caused by factors such as transfection efficiency, amount of inoculated cells, toxicity of the compound, etc, a GFP plasmid is co-transfected simultaneously as the internal reference. In the analysis of the experimental results, the luminescent values tested for all wells are calibrated with GFP values. The experimental results are expressed as relative activation fold, with a value of 1 for the solvent control. The greater the fold is, the higher the activation capacity represents.

2). Experiment Procedure

The detailed protocol for the experiment on the screening model may be found from the following reference: "Design, synthesis and evaluation of a new class of noncyclic 1,3-dicarbonyl compounds as PPARa selective activators" Bioorg Med Chem Lett. 2004; 14(13): 3507-11. The detailed procedure is described as follows:

Reagents needed: the compounds to be tested (in DMSO).

(1) Day 1: Cell Cultivation and Inoculation

Hepatocarcinoma cell HepG2 (from ATCC, American Type Culture Collection) was cultured in a DMEM medium supplemented with 10% heat-inactivated fetal bovine serum (FBS, Invitogen, Grand Island, N.Y., USA) in a T-75 culture flask (Greiner, Germany) placed in a 5% $CO_2$ incubator at 37° C. and 100% relative humidity. When the cells in the culture flask reached 80-90% confluency, it was digested with 0.25% pancreatic enzyme (with EDTA) for 3 min, and inoculated into a 96-well cell culture plate, with an inoculation density of 2000 cells/100 μl/well.

(2) Day 2: Cell Transfection

On the next day, when the cells in the 96-well culture plate grew up to 50-80% confluency, cell transfection was performed. The cell co-transfection system comprised FuGene6 transfection agent (Roche Molecular Biochemicals, Indianapolis, Ind., U.S.A.) and 60 ng DNA (10 ng hRXR, 10 ng pCMV βGal, 10 ng nuclear receptor expression plasmid RXR/PPARα, δ, γ, 30 ng GFP fluorescence reporter gene plasmid, respectively).

(3) Drug Treatment

The cell culture medium was discarded immediately after 24 hours of transfection and replaced by 200 μl fresh DMEM medium containing the test medicament (with 10% FBS treated by activated carbon). The final concentration gradients of the test medicament were 10 μM, 5 μM, 1 μM, 0.1 μM, 0.01 μM, 0.001 μM, and 0 μM. 0.05 μM 2-bromostearic acid (purchased from Sigma, USA) was used as the positive control. The final concentration of DMSO in each well was 0.1%.

(4) Kinase Activity Assay

After 24 h treatment with the medicament, the cells were lysed with a lysis solution (Cell Culture Lysis buffer, Promega) and centrifuged, and the supernatant was collected. The supernatant was reacted with a fluorescence assay kit (Promega) and counted by a fluorometer (Ascent Fluoroskan FL reader, Thermo Labsystems, Finland), and the relative intensity of luciferase was determined. For the assay of the β-galactosidase activity used in the experiment as the internal reference (the internal reference for calibrating the transfection efficiency), 50 μl of the supernatant was transferred into a fresh microplate, treated with a Promega kit, and the value was read with a microplate reader at a wavelength of 405 nm (Bio-tech Instruments Inc., Winooski, Vt., USA) (Sauerberg, P.; Olsen, G. S.; Jeppesen, L.; Mogensen, J. P. et al., J. Med. Chem., 2007, 50, 1495-1503).

3). Analysis:

The median effective concentration ($EC_{50}$) of a sample is the concentration at which the sample exerts 50% pharmacological effect, and is one of the important parameters for evaluating the pharmacological effects of a compound. In the present screening protocol, it was calculated according to the activation of the receptor by the sample at 6 different concentrations.

4). Results of the Screening Test

The results of the screening test show that the compounds of formula I of the present invention have the activity of activating peroxisome proliferator-activated receptors α, δ, and γ.

1) The Activity of the Compound of Formula I In Vitro

The activity of the compound of formula I in vitro was tested according to the following procedure:

the sample (the compound of formula I) was dissolved and diluted into various concentrations, the activity of the sample for activating PPARα, δ, γ receptors was tested according to the concentration gradients, the concentration-activity relationship was obtained, and the corresponding median effective concentration ($EC_{50}$) value was calculated.

Results:

| | PPARα | | | | | | | | | | | | |
|---|---|---|---|---|---|---|---|---|---|---|---|---|---|
| | Experiment results | | | | | | standard deviation | | | | | | $EC_{50}$ |
| Sample No. | 0.001 uM | 0.01 uM | 0.1 uM | 1 uM | 5 uM | 10 uM | 0.001 uM | 0.01 uM | 0.1 uM | 1 uM | 5 uM | 10 uM | (uM) |
| Compound 1 | 1.00 | 1.08 | 1.12 | 1.36 | 1.35 | 1.72 | 0.16 | 0.07 | 0.12 | 0.04 | 0.06 | 0.17 | 0.029 |
| Compound 2 | 1.01 | 1.06 | 1.16 | 1.30 | 1.38 | 1.82 | 0.10 | 0.10 | 0.13 | 0.03 | 0.13 | 0.08 | 5.495 |

-continued

| | PPARα | | | | | | | | | | | | |
|---|---|---|---|---|---|---|---|---|---|---|---|---|---|
| | Experiment results | | | | | | standard deviation | | | | | | $EC_{50}$ |
| Sample No. | 0.001 uM | 0.01 uM | 0.1 uM | 1 uM | 5 uM | 10 uM | 0.001 uM | 0.01 uM | 0.1 uM | 1 uM | 5 uM | 10 uM | (uM) |
| Compound 3 | 0.99 | 1.11 | 1.19 | 1.28 | 1.33 | 1.79 | 0.12 | 0.04 | 0.05 | 0.05 | 0.15 | 0.04 | 0.004 |
| Compound 4 | 1.14 | 1.20 | 1.18 | 1.65 | 2.31 | 2.96 | 0.05 | 0.05 | 0.12 | 0.21 | 0.56 | 0.52 | 5.495 |
| Compound 5 | 1.33 | 1.45 | 1.37 | 1.58 | 1.98 | 1.91 | 0.23 | 0.10 | 0.12 | 0.13 | 0.35 | 0.15 | 1.175 |
| Compound 6 | 1.33 | 1.23 | 1.27 | 1.53 | 1.76 | 1.96 | 0.12 | 0.11 | 0.04 | 0.11 | 0.45 | 0.46 | 2.630 |
| Compound 7 | 1.15 | 1.32 | 1.42 | 1.55 | 1.66 | 1.94 | 0.13 | 0.19 | 0.20 | 0.02 | 0.21 | 0.21 | 2.884 |
| Compound 8 | 1.23 | 1.35 | 1.48 | 1.41 | 1.71 | 1.93 | 0.14 | 0.10 | 0.09 | 0.16 | 0.09 | 0.30 | 5.248 |
| Compound 9 | 1.25 | 1.17 | 1.32 | 1.56 | 1.63 | 1.81 | 0.11 | 0.11 | 0.04 | 0.15 | 0.11 | 0.20 | 1.148 |
| rosiglitazone | 1.01 | 1.10 | 1.18 | 1.12 | 1.41 | 1.69 | 0.03 | 0.22 | 0.26 | 0.24 | 0.22 | 0.14 | Ia |

Ia: in-activated

| | PPARγ | | | | | | | | | | | | |
|---|---|---|---|---|---|---|---|---|---|---|---|---|---|
| | Experiment results | | | | | | standard deviation | | | | | | $EC_{50}$ |
| Sample No. | 0.001 uM | 0.01 uM | 0.1 uM | 1 uM | 5 uM | 10 uM | 0.001 uM | 0.01 uM | 0.1 uM | 1 uM | 5 uM | 10 uM | (uM) |
| Compound 1 | 1.09 | 1.21 | 1.26 | 1.45 | 1.62 | 2.01 | 0.16 | 0.18 | 0.27 | 0.14 | 0.34 | 0.09 | 0.013 |
| Compound 2 | 1.09 | 1.26 | 1.26 | 1.49 | 1.73 | 2.28 | 0.13 | 0.15 | 0.15 | 0.15 | 0.29 | 0.08 | 0.692 |
| Compound 3 | 1.10 | 1.30 | 1.32 | 1.56 | 1.78 | 2.06 | 0.13 | 0.14 | 0.12 | 0.06 | 0.20 | 0.10 | 0.005 |
| Compound 4 | 2.70 | 3.78 | 3.81 | 5.17 | 4.19 | 5.88 | 0.25 | 0.66 | 0.68 | 0.98 | 0.03 | 0.42 | 0.089 |
| Compound 5 | 1.98 | 2.99 | 3.75 | 3.95 | 3.82 | 4.11 | 0.35 | 0.26 | 0.71 | 0.50 | 0.76 | 0.47 | 0.004 |
| Compound 6 | 0.92 | 1.02 | 1.04 | 1.74 | 1.63 | 2.53 | 0.13 | 0.09 | 0.18 | 0.13 | 0.22 | 0.28 | 6.761 |
| Compound 7 | 1.29 | 1.86 | 3.30 | 3.80 | 4.08 | 4.35 | 0.12 | 0.16 | 0.41 | 0.74 | 0.73 | 0.87 | 0.025 |
| Compound 8 | 1.38 | 2.29 | 3.72 | 4.75 | 4.29 | 4.24 | 0.22 | 0.33 | 0.36 | 0.33 | 0.62 | 0.42 | 0.022 |
| Compound 9 | 1.09 | 1.51 | 3.20 | 4.34 | 5.04 | 4.26 | 0.18 | 0.14 | 0.21 | 0.23 | 0.28 | 0.26 | 0.047 |
| rosiglitazone | 1.70 | 2.49 | 4.37 | 5.00 | 5.94 | 5.79 | 0.12 | 0.05 | 0.01 | 0.40 | 0.36 | 0.15 | 0.001 |

| | PPARδ | | | | | | | | | | | | |
|---|---|---|---|---|---|---|---|---|---|---|---|---|---|
| | Experiment results | | | | | | standard deviation | | | | | | $EC_{50}$ |
| Sample No. | 0.001 uM | 0.01 uM | 0.1 uM | 1 uM | 5 uM | 10 uM | 0.001 uM | 0.01 uM | 0.1 uM | 1 uM | 5 uM | 10 uM | (uM) |
| Compound 1 | 1.07 | 1.12 | 1.19 | 1.40 | 1.33 | 1.80 | 0.14 | 0.06 | 0.04 | 0.03 | 0.15 | 0.07 | 0.029 |
| Compound 2 | 1.02 | 1.17 | 1.17 | 1.34 | 1.45 | 1.99 | 0.07 | 0.05 | 0.11 | 0.06 | 0.14 | 0.08 | <0.001 |
| Compound 3 | 1.11 | 1.17 | 1.22 | 1.34 | 1.50 | 1.94 | 0.12 | 0.08 | 0.10 | 0.03 | 0.14 | 0.07 | <0.001 |
| Compound 4 | 1.45 | 1.53 | 2.25 | 3.51 | 4.22 | 4.60 | 0.02 | 0.33 | 0.54 | 0.53 | 0.57 | 0.48 | 0.851 |
| Compound 5 | 1.57 | 2.44 | 3.61 | 3.69 | 3.57 | 4.64 | 0.27 | 0.52 | 0.88 | 0.92 | 0.25 | 0.30 | 0.007 |
| Compound 6 | 0.99 | 0.87 | 1.09 | 1.11 | 1.27 | 1.63 | 0.21 | 0.02 | 0.15 | 0.15 | 0.08 | 0.26 | 6.761 |
| Compound 7 | 1.66 | 2.72 | 2.99 | 3.70 | 3.60 | 3.38 | 0.36 | 0.41 | 0.54 | 0.64 | 0.50 | 0.20 | 0.003 |
| Compound 8 | 1.65 | 2.69 | 3.58 | 3.94 | 4.23 | 4.40 | 0.27 | 0.36 | 0.37 | 0.18 | 0.84 | 0.38 | 0.006 |
| Compound 9 | 1.18 | 1.40 | 2.25 | 3.38 | 4.08 | 3.92 | 0.12 | 0.15 | 0.25 | 0.40 | 0.21 | 0.28 | 0.331 |
| rosiglitazone | 1.39 | 1.30 | 1.48 | 1.60 | 2.85 | 3.50 | 0.06 | 0.03 | 0.12 | 0.04 | 0.17 | 0.23 | 5.248 |

The lower the $EC_{50}$ value is, the higher the activity in vitro of the compound represents.

Analysis:

The median effective concentration ($EC_{50}$) is one of the important parameters for evaluating the pharmacological effects of a compound. In the present model screening protocol, the activation of a sample on the receptor at 6 different concentrations was observed, and it can provide a general view for the pharmacological characteristics of the compound. The concentration-activity profile of the effects of a compound was fitted by carrying out iterative computation according to the following formula, and corresponding $EC_{50}$ was calculated:

$$f(x) = a + \frac{b}{c + e^{-\beta(x-\alpha)}}$$

It can be seen from the screening results that compound 1, 3, and 5 being screened have better activation effects on PPARα receptor, PPARδ receptor, and PPARγ receptor.

Structure-Activity Relationship:

| Sample No. | substituent G₃ | R₁ | EC₅₀ (uM) PPARα | PPARγ | PPARδ |
|---|---|---|---|---|---|
| Compound 1 | F— | CH₃— | 0.029 | 0.013 | 0.029 |
| Compound 2 | F₃C— | H— | 5.495 | 0.692 | <0.001 |
| Compound 3 | F₃C— | CH₃— | 0.004 | 0.005 | <0.001 |
| Compound 4 | Buᵗ— | CH₃— | 5.495 | 0.089 | 0.851 |
| Compound 5 | CH₃— | CH₃— | 1.175 | 0.004 | 0.007 |
| Compound 6 | 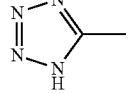 | CH₃— | 2.630 | 6.761 | 6.761 |
| Compound 7 | NO₂— | CH₃— | 2.884 | 0.025 | 0.003 |
| Compound 8 | NC— | CH₃— | 5.248 | 0.022 | 0.006 |
| Compound 9 | 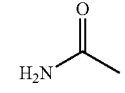 | CH₃— | 1.148 | 0.047 | 0.331 |
| rosiglitazone | | | Ia | 0.001 | 5.248 |

Ia: in-activated

It can be seen from the above table that: as for a compound of formula I, the • compounds wherein substituent G₃ is an electrophilic group have significantly better EC₅₀ for PPARα, • PPARγ • and • PPARδ than those wherein substituent G₃ is an electron donating group. In addition, the EC₅₀ is significantly related with the size of substituent G₃. The larger the substituent is, the larger the EC₅₀ is. Among others, the EC₅₀ for PPARα is influenced mostly. Furthermore, the compounds wherein substituent R₁ is methyl have significantly higher activity in vitro than those wherein R₁ is H.

2) Screening for the Activity In Vivo of Part of the Compounds of Formula (I) According to the Present Invention.

The compounds showing relatively higher activity in vitro in the screening were tested for activity in vivo. Animal models, such as ZDF rats, db/db diabetic mice, DIO obesity mice, etc., were applied, in order to determine the intervention of the medicaments.

At present, the inventors have completed the pharmacodynamic tests on 3 diabetic animal models, i.e. DB/DB, DIO, and ZDF. As for the key indicators of type II diabetes, including sugar tolerance, plasma insulin, plasma TG, etc., some compounds have similar or superior pharmacological effects on blood sugar reducing as compared with rosiglitazone. The compounds designed by the inventors also have superior cholesterol-lowering effect and body weight-lowing effect than rosiglitazone, an agonist against PPARγ only. The inventors also studied the safety of the screened compounds.

As for LD₅₀, the main indicator for evaluating acute toxicity of a medicament, most of the compounds are close to rosiglitazone (3-4 g/kg, orally). In the autopsy, no visible obvious injure was found in main visceral organs, and there was no statistical difference in the change in organ coefficient.

According to the data of the pharmacodynamic test, in combination with the toxicity test, the inventors believed that the compounds of the formula had the potential of being developed into novel medicaments for treating type II diabetes.

EXAMPLES

The present invention will be explained with reference to the following examples. It will be appreciated by those skilled in the art that the examples are not intended to limit the preparation method of the present invention.

Example 1

Preparation of 3-(2-ethyl-4-{2-[2-(4-fluorophenyl)-5-methyloxazol-4-yl]ethoxyl}phenyl)propionic acid (Compound 1)

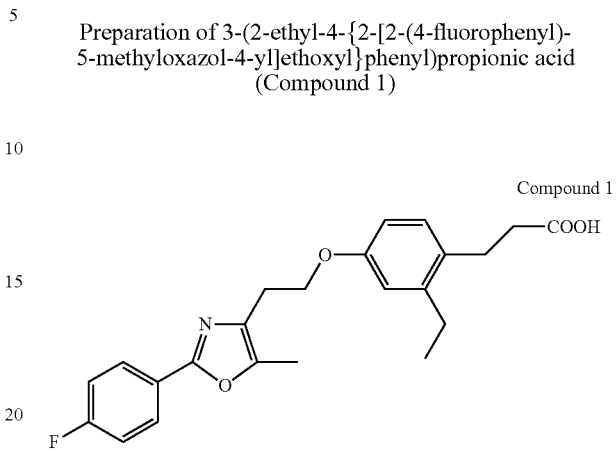

a) Preparation of 2-[2-(4-fluorophenyl)-5-methyloxazol-4-yl]ethyl methanesulfonate Step 1: Preparation of 4-carbonylpentyl benzoate 5-hydroxy-2-pentone (0.647 mol) was dissolved in dichloromethane (400 ml), 104 ml (1.294 mol) pyridine was then added. The mixture was cooled to below 10° C. in an ice-water bath, and then benzoyl chloride (90.15 ml, 0.076 mol) was slowly added dropwise maintaining the inside temperature below 10° C. It was warmed to room temperature after the addition was completed, and was stirred for 2 days for reacting. After the reaction was completed, the reaction mixture was washed with water, and extracted with dichloromethane. It was dried with anhydrous magnesium sulfate, dichloromethane was concentrated. The product was distilled under reduced pressure with an oil pump, to obtain the intermediate, i.e. 4-carbonylpentyl benzoate, with a yield of 75%.

$^1$H NMR (400 MHz, CDCl₃)ä: 2.04-2.06 (m, 2H, CH₂), 2.15 (s, 3H, CH₃), 2.58-2.61 (m, 2H, CH₂), 4.29-4.33 (m, 2H, OCH₂), 7.41-7.44 (m, 2H, ArH), 7.53-7.55 (m, H, ArH), 8.00-8.02 (m, 2H, ArH);

$^{13}$C NMR (75 MHz, CDCl₃)ä: 22.9, 30.0, 39.9, 64.1, 128.4, 129.5, 130.2, 133.0, 166.5, 207.6;

Ms(+C, ESI): M=206. Found 207 (M+1).

Step 2: Preparation of 3-bromo-4-carbonylpentyl benzoate

The intermediate, 4-carbonylpentyl benzoate (72 mmol), was dissolved in 75 ml dichloromethane. The temperature of the system was maintained below 5° C., bromine (3.7 ml, 72 mmol) was then slowly added dropwise. After the addition was completed, the stirring was maintained for half an hour, until the color of the reaction system disappears. The product was then washed with water, dried with anhydrous magnesium sulfate, and concentrated, to obtain the intermediate, i.e. 3-bromo-4-carbonylpentyl benzoate, which was directly applied in the next step without further purification.

Step 3: Preparation of 3-azido-4-carbonylpentyl benzoate

The intermediate, 3-bromo-4-carbonylpentyl benzoate (the product obtained in the previous step), was dissolved in 100 ml DMF, and then 9.3 g (143 mmol) NaN₃ was added. It was stirred overnight at room temperature. After the reaction was completed, the product was extracted with ethyl acetate, washed with water, dried with anhydrous magnesium sulfate, and then was concentrated to obtain the intermediate, i.e. 3-azido-4-carbonylpentyl benzoate, which was directly applied in the next step without further purification.

Step 4: Preparation of 3-(4-fluorobenzamido)-4-carbonylpentyl benzoate

The intermediate, 3-azido-4-carbonylpentyl benzoate (the product obtained in the previous step), was dissolved in 200 ml methanol, 2 g palladium on carbon catalyst for hydrogenation was added, and then hydrogen was bubbled through the solution. After the reaction was completed, the palladium on carbon was filtered off, and the product was concentrated to obtain the intermediate, i.e. 3-amine-4-carbonylpentyl benzoate. The intermediate, 3-amine-4-carbonylpentyl benzoate, was dissolved in 200 ml ethyl acetate, cooled to 0° C., potassium carbonate (30 g, 216 mmol) was added, and p-fluorobenzoyl chloride (72 mmol) was added dropwise maintaining the temperature below 5° C. After the reaction was completed, the product was washed with water and extracted with ethyl acetate. The organic phase was dried with anhydrous magnesium sulfate, and was concentrated, to obtain the intermediate, i.e. crude 3-(4-fluorobenzamido)-4-carbonylpentyl benzoate. The crude product was separated and purified, to obtain 16.1 g the intermediate, with a yield of 65% (the total yield from the 3 steps, i.e. step 2, step 3, and step 4).

$^1$H NMR (400 MHz, CDCl₃)ä: 2.32-2.41 (m, 4H, CH₃ and CH₂), 2.58-2.65 (m, H, CH₂), 4.30 (t, J=6.0 Hz, 2H, OCH₂), 4.92 (m, 1H, NCH), 7.08-7.12 (m, 2H, ArH), 7.27 (s, br, H, NH), 7.41-7.45 (m, 2H, ArH), 7.53-7.59 (m, H, ArH), 7.85 (d, J=8.4 Hz, 2H, ArH), 7.95 (d, J=8.4 Hz, 2H, ArH);

Ms(+C, ESI): M=343. Found 344 (M+1).

Step 5: Preparation of 2-[2-(4-fluorophenyl)-5-methyloxazol-4-yl]ethyl benzoate The intermediate, 3-(4-fluorobenzamido)-4-carbonylpentyl benzoate (15.4 g, 45 mmol) obtained in the previous step, was dissolved in 350 ml toluene, and phosphorus oxychloride (8.5 ml, 90 mmol) was slowly added dropwise at room temperature. After addition was completed, the mixture was heated for 2.5 hours under refluxing. After the reaction was completed, the reaction solution was poured into ice-water mixture, extracted with toluene, concentrated, and then separated and purified, to obtain the intermediate, i.e. 2-[2-(4-fluorophenyl)-5-methyloxazol-4-yl]ethyl benzoate (13.2 g, with a yield of 90%).

$^1$H NMR (400 MHz, CDCl₃)ä: 2.33 (s, 3H, CH3), 2.96 (t, J=6.4 Hz 2H, CH2), 4.59 (t, J=6.4 Hz, 2H, OCH2), 7.09-7.13 (m, 2H, ArH), 7.41-7.44 (m, 2H, ArH), 7.53-7.55 (m, H, ArH), 7.95-8.03 (m, 4H, ArH);

$^{13}$C NMR (75 MHz, CDCl₃)ä: 10.2, 25.8, 63.7, 115.7, 115.9, 124.1, 124.2, 127.9, 128.0, 128.4, 129.6, 130.3, 132.5, 132.9, 144.9, 158.8, 162.5, 165.0, 166.5;

Ms(+C, ESI): M=325. Found 326 (M+1).

Step 6: Preparation of 2-[2-(4-fluorophenyl)-5-methyloxazol-4-yl]ethanol

The intermediate, 2-[2-(4-fluorophenyl)-5-methyloxazol-4-yl]ethyl benzoate (19.5 g, 60 mmol) was dissolved in 70 ml ethanol and stirred. 10% sodium hydroxide solution (NaOH: 4.8 g, 120 mmol) was slowly added dropwise, and the mixture was stirred overnight at room temperature. After the reaction was completed, the ethanol was concentrated, and the product was extracted with toluene, and then was washed with water and brine sequently, dried with anhydrous magnesium sulfate, and concentrated to obtain the intermediate, i.e. 2-[2-(4-fluorophenyl)-5-methyloxazol-4-yl]ethanol, which was directly applied in the next step without further purification.

Step 7: Preparation of 2-[2-(4-fluorophenyl)-5-methyloxazol-4-yl]ethyl methanesulfonate The intermediate, 2-[2-(4-fluorophenyl)-5-methyloxazol-4-yl]ethanol (the product obtained in the previous step), was dissolved in 200 ml dichloromethane, and then was cooled to 0° C. Triethylamine (100 mmol) was added at this temperature, and MsCl (60 mmol) was slowly added dropwise. After the addition was completed, the mixture was warmed to room temperature, and was stirred overnight. After the reaction was completed, the product was washed with water, extracted with dichloromethane, dried with anhydrous magnesium sulfate, concentrated, separated, and purified, to obtained the compound 2-[2-(4-fluorophenyl)-5-methyloxazol-4-yl]ethyl methane sulfonate (15.6 g, with a yield of 87% from the 2 steps).

$^1$H NMR (400 MHz, CDCl₃)ä: 2.32 (s, 3H, CH₃), 2.91-2.96 (m, 5H, CH₂ and SO₂CH₃), 4.51 (t, 2H, OCH₂), 7.09-7.13 (m, 2H, ArH), 7.92-7.94 (m, H, ArH);

$^{13}$C NMR (75 MHz, CDCl₃)ä: 10.1, 26.2, 37.2, 116.0, 123.9, 128.0, 131.1, 145.5, 158.9, 162.5, 162.6, 165.0;

Ms(+C, ESI): M=299. Found 300 (M+1).

b) Preparation of ethyl 3-(2-ethyl-4-hydroxylphenyl)propionate

The compound can be prepared with reference to the disclosure of the patent reference WO/2005/054176.

c) Preparation of ethyl 3-(2-ethyl-4-{2-[2-(4-fluorophenyl)-5-methyloxazol-4-yl]ethoxy}phenyl)propionate and 3-(2-ethyl-4-{2-[2-(4-fluorophenyl)-5-methyloxazol-4-yl]ethoxy}phenyl)propionic acid The parent phenolic compound, ethyl 3-(2-ethyl-4-hydroxylphenyl)propionate (10.4 g, 50 mmol) and 120 ml acetonitrile were added into a 250 ml single neck flask, and stirred. Then the parent sulfonate compound, 2-[2-(4-fluorophenyl)-5-methyloxazol-4-yl]ethyl methanesulfonate (15 g, 50 mmol) and potassium carbonate (K₂CO₃) (100 mmol) were added. The mixture was heated for 16 hours under reflux. After the reaction was completed, the product was filtered. The filter cake was washed with ethyl acetate (3×50 ml) and then discarded. The filtrates were combined, and the solvent was distilled off under reduced pressure, to obtain crude ethyl 3-(2-ethyl-4-{2-[2-(4-fluorophenyl)-5-methyloxazol-4-yl]ethoxy}phenyl)propionate. The crude ethyl 3-(2-ethyl-4-{2-[2-(4-fluorophenyl)-5-methyloxazol-4-yl]ethoxy}phenyl)propionate, without purification, was dissolved with 120 ml ethanol. 10% NaOH (30 ml) was added at room temperature, and the stirring was maintained for 3 hours at room temperature. After the reaction was completed, the product was acidified by adding 10% dilute hydrochloric acid, to obtain a solid precipitate. It was filtered by suction filtration, to obtain crude 3-(2-ethyl-4-{2-[2-(4-fluorophenyl)-5-methyloxazol-4-yl]ethoxy}phenyl)propionic acid.

The crude product was crystallized by ethyl acetate-petroleum ether, to obtain 12.3 g white solid, with a yield of 62% from the 2 steps.

¹H NMR (400 MHz, CDCl₃)ä: 1.22 (t, J=7.6 Hz 3H, CH₃), 2.37 (s, 3H, CH₃), 2.59-2.65 (m, 4H, 2CH₂), 2.90-2.94 (m, 2H, CH₂), 2.97 (t, J=6.4 Hz, 2H, CH₂), 4.22 (t, J=6.4 Hz, 2H, OCH₂), 6.69-6.76 (m, 2H, ArH), 7.05-7.15 (m, 3H, ArH), 7.96-7.98 (m, 2H, ArH);

¹³C NMR (75 MHz, CDCl₃)ä: 10.2, 15.1, 25.7, 26.3, 26.7, 35.4, 66.6, 111.7, 114.9, 115.0, 115.7, 115.9, 124.0, 128.1, 130.0, 132.7, 143.3, 145.1, 157.5, 158.8, 162.5, 165.0, 179.1;

Ms(+C, ESI): M=397. Found 398 (M+1), 420 (M+Na).

Example 2

The following compounds were obtained by using corresponding starting materials, according to the method in example 1.

Compound 2, white solid, yield: 63%

¹H NMR (400 MHz, CDCl₃)ä: 1.22 (t, J=7.6 Hz 3H, CH₃), 2.59-2.65 (m, 4H, 2CH₂), 2.89-2.93 (m, 2H, CH₂), 3.09 (t, J=6.4 Hz, 2H, CH₂), 4.27 (t, J=6.4 Hz, 2H, OCH₂), 6.70-6.73 (m, 2H, ArH), 6.77 (d, J=2.4 Hz, 1H, ArH), 7.07 (d, J=8.4 Hz, 1H, ArH), 7.62 (s, 1H, OCH=), 7.70 (d, J=8.4 Hz, 2H, ArH), 8.13 (d, J=8.4 Hz, 2H, ArH);

¹³C NMR (75 MHz, CDCl₃)ä: 15.1, 25.7, 26.7, 26.9, 35.2, 66.0, 111.7, 115.1, 125.7, 125.8, 126.7, 129.4, 130.2, 130.6, 136.1, 139.4, 143.4, 157.4, 178.0;

Ms(+C, ESI): M=433. Found 438 (M+1), 456 (M+Na).

compound 3, white solid, yield: 58%

¹H NMR (400 MHz, CDCl₃)ä: 1.20 (t, J=7.6 Hz 3H, CH₃), 2.40 (s, 3H, CH₃), 2.57-2.64 (m, 4H, 2CH₂), 2.88-2.92 (m, 2H, CH₂), 2.98 (t, J=6.4 Hz, 2H, CH₂), 4.22 (t, J=6.4 Hz, 2H, OCH₂), 6.67-6.74 (m, 2H, ArH), 6.73 (d, J=2.4 Hz, 1H, ArH), 7.67 (d, J=8.4 Hz, 2H, ArH), 8.08 (d, J=8.4 Hz, 2H, ArH);

¹³C NMR (75 MHz, CDCl₃)ä: 10.3, 15.2, 25.7, 26.3, 26.7, 35.5, 66.5, 111.7, 115.0, 125.6, 125.7, 126.1, 129.7, 130.0, 130.8, 131.2, 133.5, 143.3, 146.1, 157.4, 158.2, 178.7;

Ms(+C, ESI): M=447. Found 448 (M+1), 470 (M+Na).

compound 4, white solid, yield: 72%

¹HNMR (400 MHz, CDCl₃)ä: 1.17 (t, j=7.6 HZ, 3H, CH₃), 1.27 (s, 9H, C(CH₃)₃), 2.35 (s, 3H, CH₃), 2.57 (m, 4H, 2CH₂), 2.86 (m, 2H, CH₂), 2.96 (t, J=6.4 Hz, 2H, CH₂), 4.17 (t, J=6.4 Hz, 2H, —OCH₂), 6.67 (m, 2H, ArH), 7.02 (d, J=4.0 Hz, 1H, ArH), 7.43 (d, J=4.4 Hz, 2H, ArH), 7.89 (d, J=4.4 Hz, 2H, ArH);

¹³CNMR (100 MHz, CDCl₃)ä: 10.2, 15.1, 25.6, 26.2, 26.8, 31.1 (3C), 34.8, 35.6, 66.5, 111.5, 114.8, 124.6, 125.6 (2C), 125.7 (2C), 129.6, 130.0, 132.3, 143.2, 144.7, 153.1, 157.3, 159.6, 178.5;

Ms(+C, ESI): M=435. Found 436 (M+1).

compound 5, white solid, yield: 71%

¹H NMR (400 MHz, CDCl₃)ä: 1.19 (t, J=7.6 Hz, 3H, CH₃), 2.35 (s, 3H, CH₃), 2.37 (s, 3H, CH₃), 2.59 (m, 4H, 2CH₂), 2.88 (t, J=7.6 Hz, 2H, CH₂), 2.96 (t, J=6.4 Hz, 2H, CH₂), 4.18 (t, J=6.4 Hz, 2H, OCH₂), 6.68 (m, 2H, ArH), 7.03 (d, J=8.0 Hz, 1H, ArH), 7.23 (d, J=8.0 Hz, 2H, ArH), 7.85 (d, J=7.6 Hz, 2H, ArH);

¹³C NMR (100 MHz, CDCl₃)ä: 10.3, 15.2, 21.5, 25.7, 26.2, 26.9, 35.7, 66.6, 111.6, 114.9, 124.7, 126.0 (2C), 129.4 (2C), 129.7, 130.1, 132.3, 140.2, 143.3, 144.8, 157.4, 159.8, 178.3;

Ms(+C, ESI): M=393. Found 394 (M+1).

compound 6, white solid, yield: 62%

¹H NMR (400 MHz, d-DMSO)ä: 1.11 (t, J=7.6 Hz 3H, CH₃), 2.35 (s, 3H, CH₃), 2.43-2.63 (m, 4H, 2CH₂), 2.74 (t, J=6.4 Hz, 2H, CH₂), 2.90 (t, J=6.4 Hz, 2H, CH₂), 4.17 (t, J=6.4 Hz, 2H, OCH₂), 6.61-6.68 (m, 2H, ArH), 6.70 (d, J=2.4 Hz, 1H, ArH), 7.67 (d, J=8.4 Hz, 2H, ArH), 8.08 (d, J=8.4 Hz, 2H, ArH);

$^{13}$C NMR (100 MHz, d-DMSO)ä: 9.8, 15.1, 25.0, 25.6, 26.2, 35.0, 65.9, 111.5, 114.4, 126.1, 127.3, 128.7, 129.5, 130.2, 133.2, 142.8, 145.6, 155.6, 156.7, 157.5, 173.8;

Ms(+C, ESI): M=447. Found 448 (M+1), 470 (M+Na).

compound 7, white solid, yield: 70%

$^1$H NMR (400 MHz, d-DMSO)ä: 1.20 (t, J=7.6 Hz 3H, CH$_3$), 2.42 (s, 3H, CH$_3$), 2.57-2.61 (m, 4H, 2CH$_2$), 2.89 (t, J=7.6 Hz, 2H, CH$_2$), 2.99 (t, J=6.4 Hz, 2H, CH$_2$), 4.21 (t, J=6.4 Hz, 2H, OCH$_2$), 6.67-6.73 (m, 2H, ArH), 7.05 (d, J=8.0 Hz, 1H, ArH), 8.13 (d, J=8.0 Hz, 2H, ArH), 8.29 (d, J=7.6 Hz, 2H, ArH);

$^{13}$C NMR (100 MHz, d-DMSO)ä: 9.8, 15.0, 25.0, 25.5, 26.2, 35.0, 65.7, 111.4, 114.3, 124.1, 126.2, 129.4, 130.2, 132.2, 134.0, 142.7 146.9, 147.5, 156.4, 156.6, 173.9;

Ms(+C, ESI): M=424. Found 425 (M+1), 447 (M+Na).

compound 8, white solid, yield: 52%

$^1$H NMR (400 MHz, CDCl$_3$)ä: 0.87 (t, J=7.6 Hz 3H, CH$_3$), 2.40 (s, 3H, CH$_3$), 2.59-2.61 (m, 4H, 2CH$_2$), 2.74-2.98 (m, 4H, 2CH$_2$), 4.20 (t, J=6.4 Hz, 2H, OCH$_2$), 6.66-6.72 (m, 2H, ArH), 7.05 (d, J=2.4 Hz, 1H, ArH), 7.70 (d, J=8.4 Hz, 2H, ArH), 8.06 (d, J=8.4 Hz, 2H, ArH);

$^{13}$C NMR (100 MHz, CDCl$_3$)ä: 10.3, 15.2, 25.6, 26.3, 26.7, 35.4, 66.4, 111.6, 112.9, 114.9, 118.5, 126.2, 129.7, 130.0, 131.3, 132.5, 133.9, 143.3, 146.7, 157.3, 157.6, 178.5;

Ms(+C, ESI): M=404. Found 405 (M+1), 427 (M+Na).

compound 9, white solid, yield: 64% $^1$H NMR (400 MHz, CDCl$_3$)ä: 1.12 (t, J=7.2 Hz 3H, CH$_3$), 2.37 (s, 3H, CH$_3$), 2.43 (t, J=7.2 Hz, 2H, CH$_2$), 2.51-2.56 (m, 4H, 2CH$_2$), 2.72 (t, J=7.2 Hz, 2H, CH$_2$), 2.91 (m, 2H, CH$_2$), 4.17 (t, J=7.2 Hz, 2H, OCH$_2$), 6.68-6.70 (m, 2H, ArH), 7.04 (d, J=7.6 Hz, 1H, ArH), 7.51 (s, br, 1H, ArH), 7.93-8.04 (m, 4H, ArH), 8.12 (s, br, 1H, ArH);

$^{13}$C NMR (100 MHz, CDCl$_3$)ä: 9.8, 15.2, 25.0, 25.6, 26.3, 35.1, 65.9, 111.6, 114.5, 125.2, 128.2, 129.2, 129.6, 130.3, 133.0, 135.2, 142.8, 145.7, 156.7, 157.7, 167.2, 173.9;

Ms(+C, ESI): M=422. Found 423 (M+1), 445 (M+Na).

compound 10, white solid, yield: 65%

$^1$H NMR (400 MHz, CDCl$_3$)ä: 1.21 (t, J=7.6 Hz 3H, CH$_3$), 2.58-2.64 (m, 4H, 2CH$_2$), 2.89-2.93 (m, 2H, CH$_2$), 3.07 (t, J=6.4 Hz, 2H, CH$_2$), 4.25 (t, J=6.4 Hz, 2H, OCH$_2$), 6.69-6.77 (m, 2H, ArH), 7.06-7.15 (m, 3H, ArH), 7.55 (s, 1H, OCH=), 7.98-8.02 (m, 2H, ArH);

$^{13}$C NMR (75 MHz, CDCl$_3$)ä: 15.2, 25.7, 26.7, 26.8, 35.4, 66.1, 111.7, 115.0, 115.8, 116.1, 123.8, 128.5, 129.7, 130.2, 135.3, 138.9, 143.4, 157.4, 160.8, 162.8, 165.3, 178.5;

Ms(+C, ESI): M=383. Found 384 (M+1).

compound 11, white solid, yield: 54%

$^1$H NMR (400 MHz, CDCl$_3$)ä: 1.22 (t, J=7.6 Hz 3H, CH$_3$), 1.33 (t, J=7.6 Hz 3H, CH$_3$), 2.59-2.66 (m, 4H, 2CH$_2$), 2.79 (q, J=7.6 Hz 2H, CH$_2$), 2.90-2.94 (m, 2H, CH$_2$), 3.01 (t, J=6.4 Hz, 2H, CH$_2$), 4.23 (t, J=6.4 Hz, 2H, OCH$_2$), 6.69-6.75 (m, 2H, ArH), 7.07 (d, J=7.2 Hz, 1H, ArH), 7.70 (d, J=8.0 Hz, 2H, ArH), 8.11 (d, J=8.0 Hz, 2H, ArH);

Ms(+C, ESI): M=461. Found 462 (M+1), 484 (M+Na).

The invention claimed is:

1. A compound of formula (I) or pharmaceutical acceptable salts thereof:

wherein,
X is O;
Y is O;
R$_1$ is methyl;
G$_1$ is ethyl; and
G$_2$ is H, and G$_3$ is F.

2. A pharmaceutical composition, comprising the compound according to claim 1 or pharmaceutical acceptable salts thereof.

3. The pharmaceutical composition according to claim 2, with a dosage form selected from tablets, film-coated tablets, sugar coated tablets, enteric coated tablets, dispersible tablets, capsules, granules, oral solutions and oral suspensions.

4. A method for treatment of diseases associated with α subtype, δ subtype, and γ subtype of peroxisome proliferator-activated receptors in a subject, the method comprising administering to the subject a compound according to claim 1, and wherein the diseases associated with α subtype, δ subtype, and γ subtype of peroxisome proliferator-activated receptors are selected from hyperglycaemia, insulin resistance, hyperlipidemia and obesity.

5. A method for the preparation of the compound of formula (I) according to claim 1, including

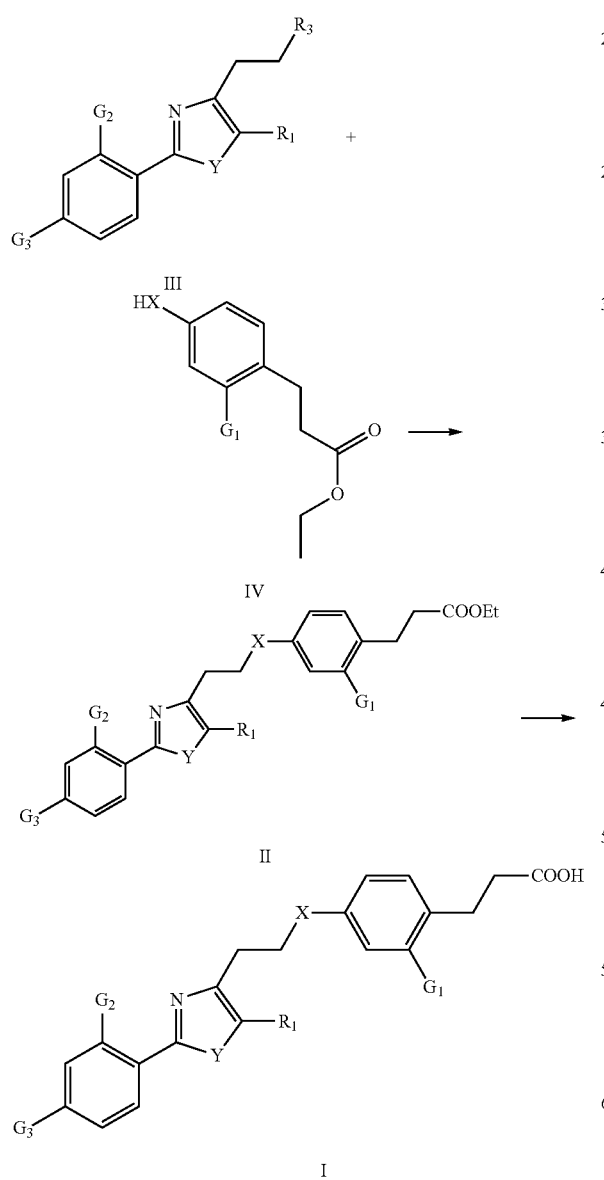

wherein,
X, Y, $R_1$, $G_1$, $G_2$, and $G_3$ are as defined in claim 1, $R_3$ is a leaving group selected from OH, Cl, Br, I, OTs and OMs.

6. The method according to claim 5, further comprising heating the compound of formula (III) and the compound of formula (IV) in acetonitrile under reflux in the presence of potassium carbonate; to obtain the compound of formula (II); saponifying the compound of formula (II) in an alcoholic solution in the presence of an alkali; and acidifying the reaction mixture after the reaction is completed; to obtain the compound of formula (I).

7. A method of making a compound of formula (I) or pharmaceutical acceptable salts thereof:

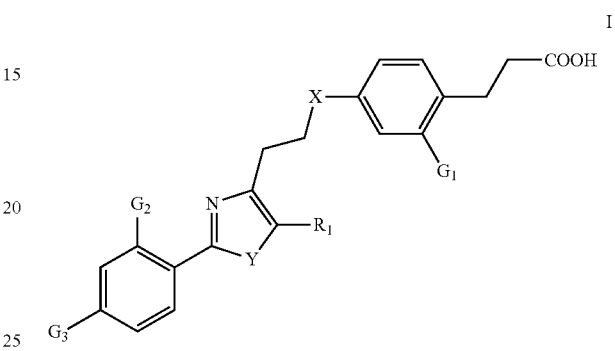

wherein,
X is O, S, $NR_{11}$, or $(CR_{11}R_{11'})_n$, in which n is an integer selected from 1, 2, 3 and 4;
Y is O, S, $NR_{11}$, or $(CR_{11}R_{11'})_m$, in which m is an integer selected from 1, 2, 3 and 4;
$R_1$ is independently H, methyl or ethyl;
$G_1$ is ethyl;
$G_2$ and $G_3$ are each independently selected from H, alkyl, alkoxy, trifluoromethyl, halogen, nitro, $NR_{11}R_{11'}$, alkylthio, amido, cyano, carboxyl and tetrazolyl;
$R_{11}$ and $R_{11'}$ are each independently selected from H and $C_1$-$C_6$ alkyl, comprising the following steps by reacting compound (III) with compound (IV) to generate compound (II), and then compound (I):

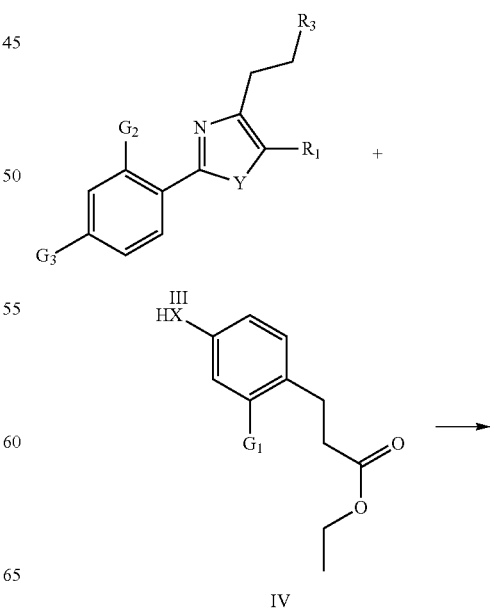

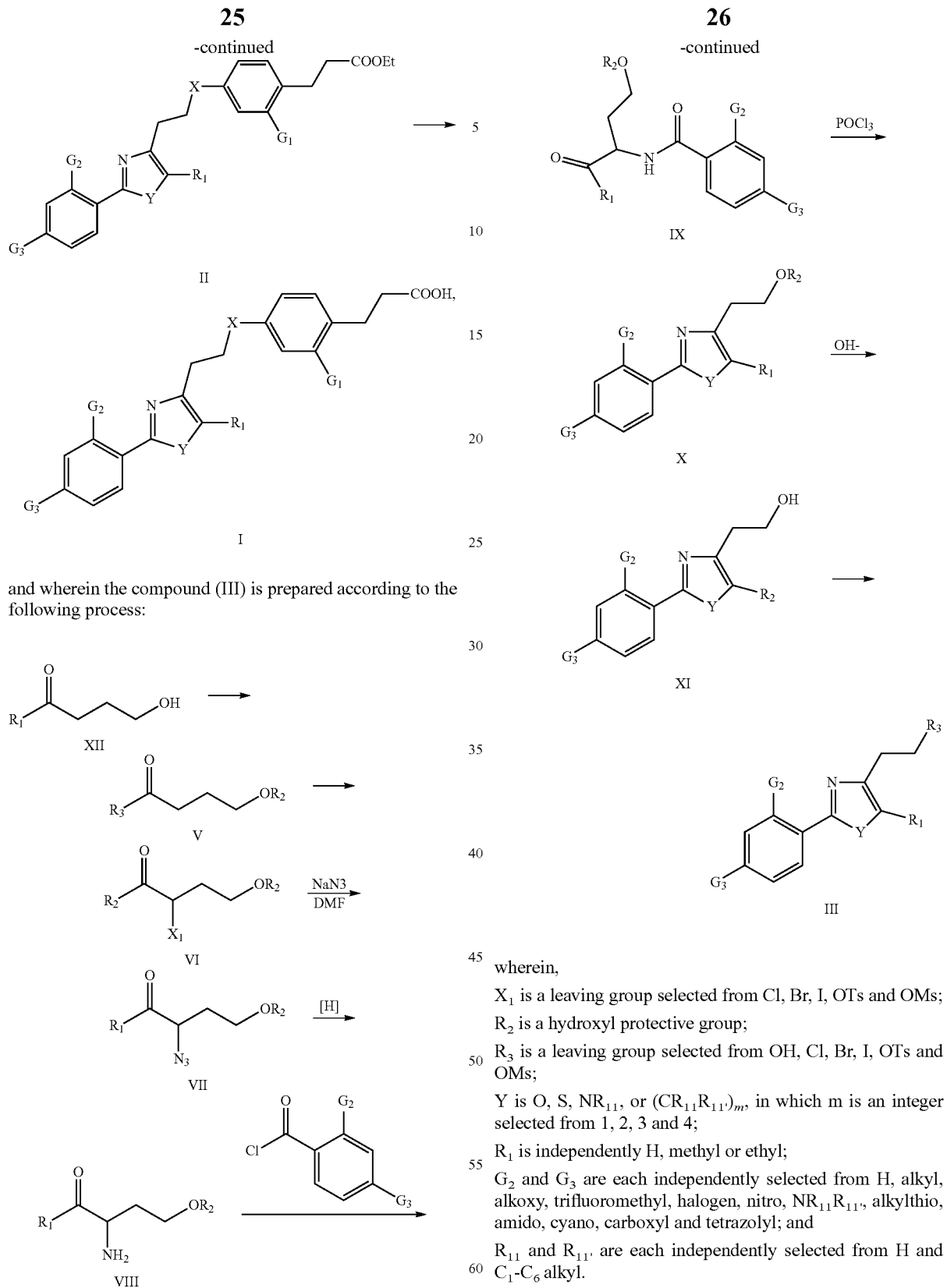

and wherein the compound (III) is prepared according to the following process:

wherein, $X_1$ is a leaving group selected from Cl, Br, I, OTs and OMs;

$R_2$ is a hydroxyl protective group;

$R_3$ is a leaving group selected from OH, Cl, Br, I, OTs and OMs;

Y is O, S, $NR_{11}$, or $(CR_{11}R_{11'})_m$, in which m is an integer selected from 1, 2, 3 and 4;

$R_1$ is independently H, methyl or ethyl;

$G_2$ and $G_3$ are each independently selected from H, alkyl, alkoxy, trifluoromethyl, halogen, nitro, $NR_{11}R_{11'}$, alkylthio, amido, cyano, carboxyl and tetrazolyl; and $R_{11}$ and $R_{11'}$ are each independently selected from H and $C_1$-$C_6$ alkyl.

* * * * *